US00PP16349P3

(12) United States Plant Patent
Holland

(10) Patent No.: US PP16,349 P3
(45) Date of Patent: Mar. 14, 2006

(54) LILAC PLANT NAMED 'BAILMING'

(50) Latin Name: ***Syringa meyeri*×*Syringa microphylla***
Varietal Denomination: Bailming

(75) Inventor: Neal S. Holland, Harwood, ND (US)

(73) Assignee: Bailey Nurseries, Inc., St. Paul, MN (US)

( * ) Notice: Subject to any disclaimer, the term of this patent is extended or adjusted under 35 U.S.C. 154(b) by 88 days.

(21) Appl. No.: 10/769,779

(22) Filed: Feb. 3, 2004

(65) Prior Publication Data

US 2005/0172376 P1 Aug. 4, 2005

(51) Int. Cl.
*A01H 5/00* (2006.01)

(52) U.S. Cl. ..... Plt./248

(58) Field of Classification Search ..... Plt./248
See application file for complete search history.

*Primary Examiner*—Kent Bell
*Assistant Examiner*—Louanne Krawczewicz Myers
(74) *Attorney, Agent, or Firm*—Buchanan Ingersoll PC

(57) ABSTRACT

A new and distinct highly ornamental cultivar of *Syringa meyeri*×*Syringa microphylla* is provided. A Lilac plant having a rounded uniform compact growth habit is described. Highly attractive trusses of fragrant red purple blossoms are formed in late spring that fade to lavender pink. The plant has good winter hardiness and has been found to be relatively free of insect and disease problems during observations to date. The plant is particularly well-suited for growing as an ornamental specimen or as a mass planting in the landscape.

2 Drawing Sheets

Figure 1:
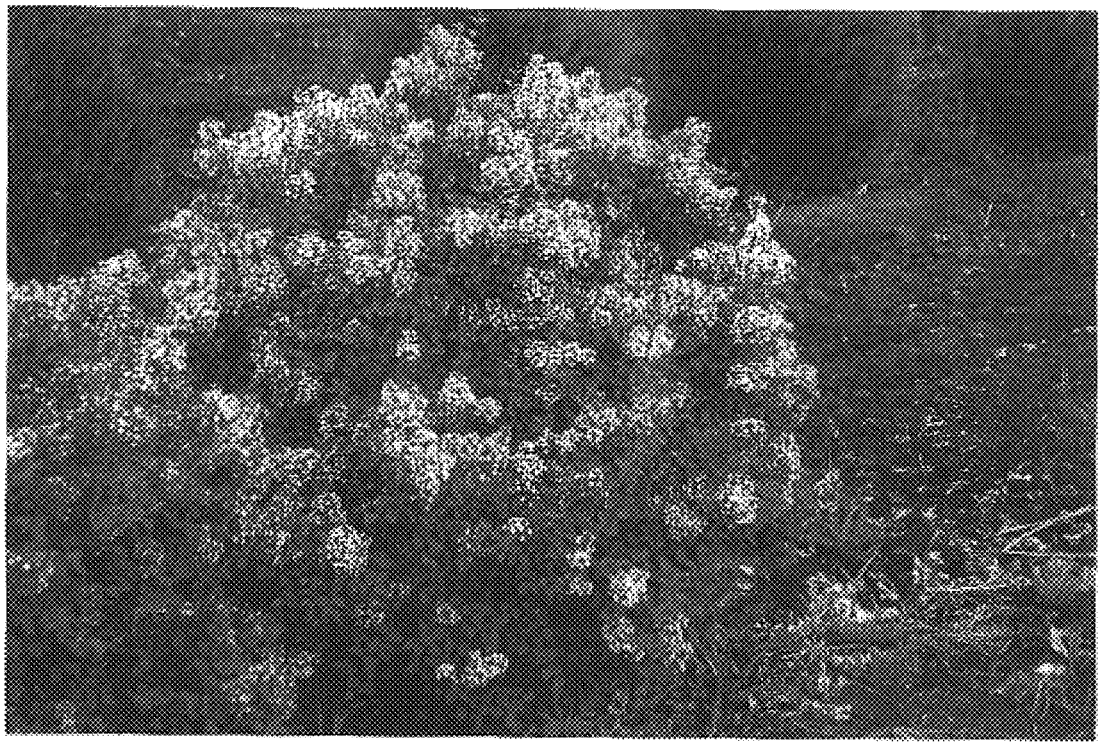

Botanical commercial classification: *Syringa meyeri*×*Syringa microphylla*/Ornamental Lilac Shrub.
Varietal denomination: cv. 'Bailming'.

SUMMARY OF THE INVENTION

The new Lilac plant of the present invention was created at Harwood, N. Dak., U.S.A., by the cross of *Syringa meyeri* 'Palibin' (non-patented in the United States) and *Syringa microphylla* 'Superba' (non-patented in the United States). The parentage can be summarized as follows:

'Palibin'×'Superba'.

Seeds from the cross were collected during 1976, were planted, and the resulting plants were observed. A single plant of new cultivar was selected during 1985 in view of its distinctive combination of ornamental characteristics. This plant initially was designated No. 92-1.

It was found that the cultivar of *Syringa meyeri*×*Syringa microphylla* exhibits the following combination of characteristics:

(a) exhibits a rounded uniform compact growth habit, (b) forms attractive trusses of fragrant red purple blossoms in late spring that fade to lavender pink, (c) is relatively free of insect and disease problems, and (d) is well-suited for growing as a distinctive ornamental shrub in the landscape.

The new cultivar of the present invention provides a distinctive red purple blossom coloration to the landscape that is displayed in late spring after many other shrubs have finished flowering. It can be grown to advantage as a specimen shrub or in a mass planting. The plant is versatile for many uses in the landscape including foundation plantings and informal hedges. The superior hardiness of the *Syringa meyeri* 'Palibin' parent which generally is lacking in the *Syringa microphylla* 'Superba' parent is imparted to the new cultivar of the present invention.

The new cultivar of the present invention can be readily distinguished from its parental cultivars. More specifically, the 'Palibin' cultivar exhibits a low spreading growth habit and the blossoms open to a pale lilac coloration, and the 'Superba' cultivar exhibits a taller and considerably more spreading growth habit and forms deep pink blossoms.

The new cultivar of the present invention also can be readily distinguished from other Lilac cultivars, such as 'Bailbelle' (U.S. Plant Pat. No. 12,294), 'Baildust' (U.S. Plant Pat. No. 15,152), and 'Bailsugar' (U.S. Plant Pat. No. 15,588), resulting from the same breeding program in view of the distinctive blossom coloration. More specifically, the 'Bailbelle' variety forms pink blossoms, the 'Baildust' variety forms pale antique pink blossoms, and the 'Bailsugar' variety forms purple lilac blossoms. The red purple blossoms of the new variety fade to an attractive lavender pink.

The new cultivar of the present invention was asexually propagated by the use of rooted cuttings and grafting at St. Paul, Minn., U.S.A., during 1992, and the progeny were field planted during 1993. The distinctive characteristics of the new cultivar have been found to be stable and to be capable of transmission from one generation to another following such asexual propagation at St. Paul, Minn. and elsewhere. The new cultivar reproduces true to type in successive generations of asexual reproduction.

The new cultivar of the present invention also has been grafted on *Syringa reticulata* to form distinctive small grafted trees.

The new cultivar of the present invention has been named 'Bailming'. It is a member of the FAIRYTALE™ Series of Lilac plants that includes the 'Bailbelle' 'Baildust' and 'Bailsugar' cultivars, and is being marketed under the PRINCE CHARMING trademark.

BRIEF DESCRIPTION OF THE PHOTOGRAPHS

The accompanying photographs show, as true as reasonably possible to make the same in color illustrations of this character typical plants of the new cultivar. The plants were propagated by use of rooted cuttings and were photographed when approximately three years of age while growing outdoors during late spring at St. Paul, Minn., U.S.A.

FIG. 1—shows a blossoming plant wherein the uniformly rounded and compact growth habit of the new cultivar is exhibited.

Figure 2:
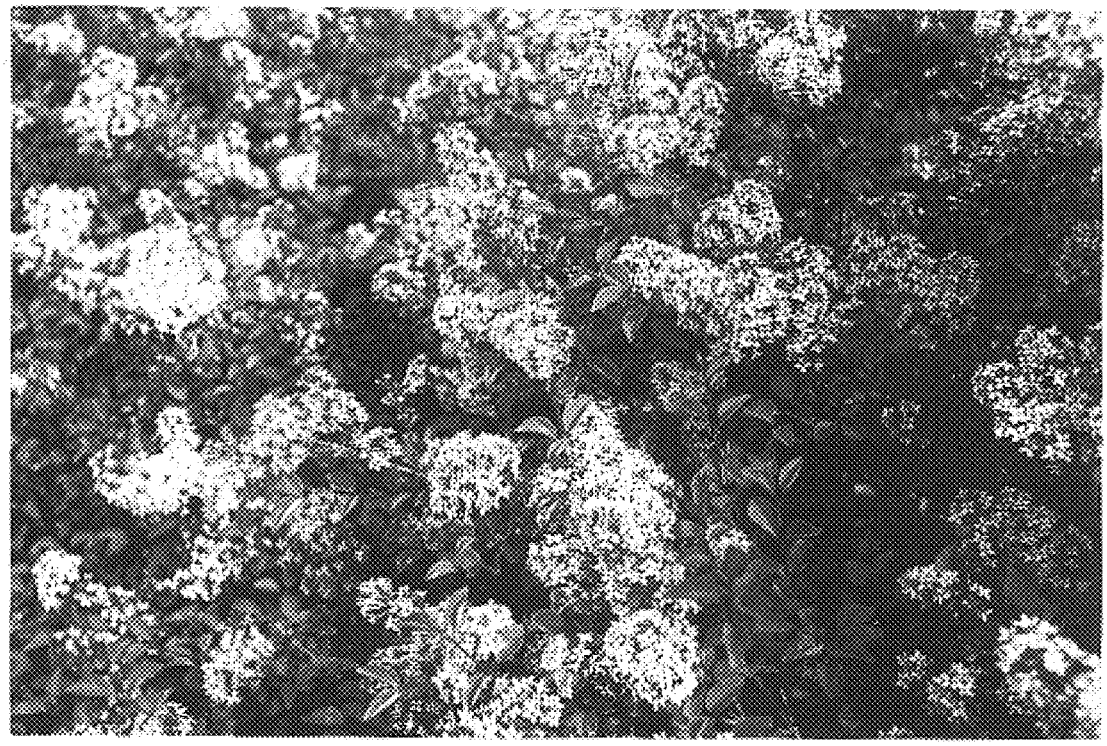

FIG. 2—shows a closer view of the red purple blossoms that fade to lavender pink as well as the foliage.

Figure 3:
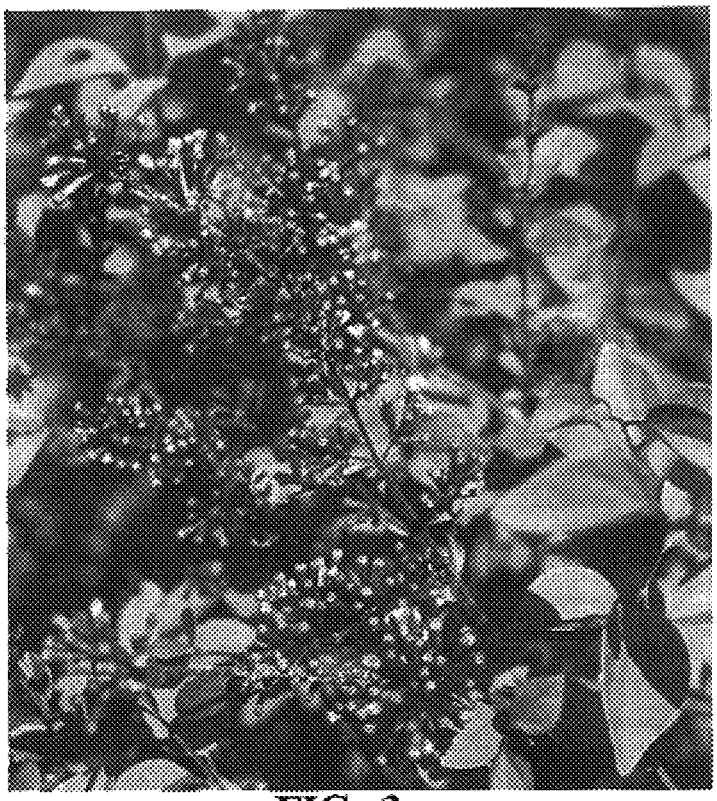

FIG. 3—shows the distinctive wine red buds with attractive foliage.

Figure 4:
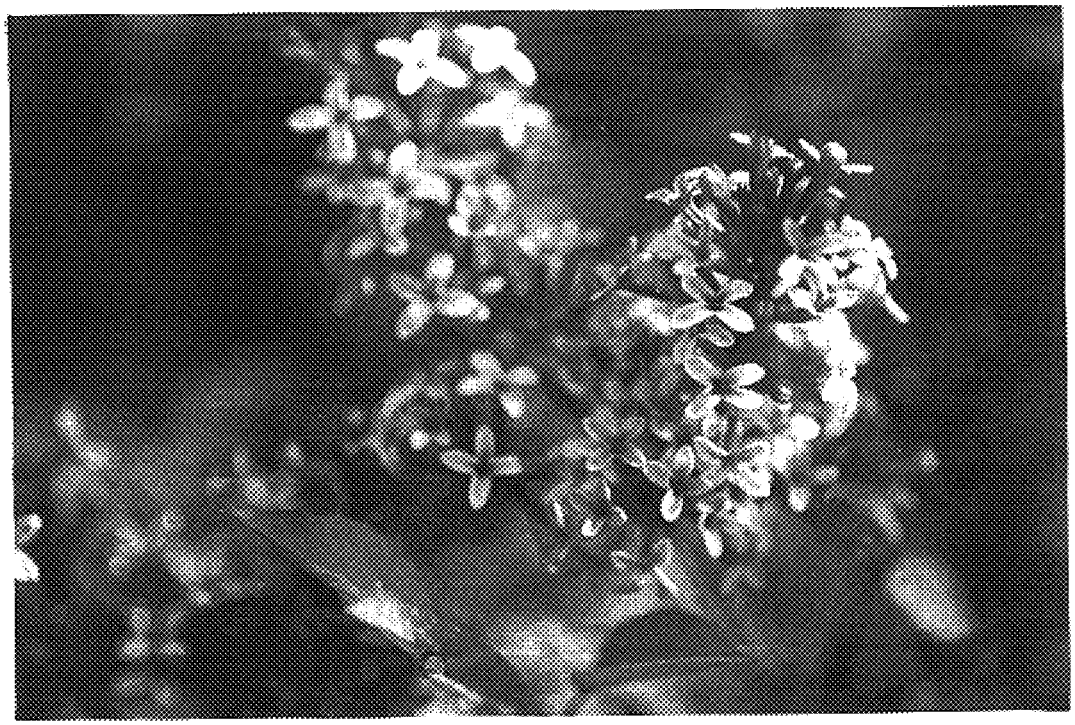

FIG. 4—shows a close-up view of the open blossoms with some foliage.

DETAILED DESCRIPTION

The chart used in the identification of colors is The R.H.S. Colour Chart of The Royal Horticultural Society, London, England. Common terms are to be accorded their ordinary dictionary significance. The description is based upon the observation during July 2002 and 2003 of five year-old plants propagated by the use of rooted cuttings and growing in containers and in the field at St. Paul, Minn., U.S.A.

Botanical classification: *Syringa meyeri*×*Syringa microphylla,* cv. 'Bailming'.

Plant:

*Growth habit.*—Neat compact rounded shrub, and a uniform grower.

*Size.*—Forms a shrub of approximately 1.5 to 1.8 m in height and approximately 1.25 to 1.8 m width.

Bark:

*Texture.*—Glabrous.

*Color.*—Grey-Brown Group 199B.

Foliage:

*Leaf shape.*—Elliptic/ovate.

*Arrangement.*—Opposite.

*Leaf length.*—Approximately 4.25 cm on average.

*Leaf width.*—Approximately 3.5 cm on average.

*Leaf apex.*—Acute to obtuse.

*Leaf base.*—Rounded.

*Leaf surface.*—Matte.

*Leaf margins.*—Entire.

*Venation.*—Palmately-veined.

*Color.*—Yellow-Green Group 146A blending with Red-Purple Group 59B at the margin (upper surface) and Yellow-Green Group 146B suffused with Red-Purple Group 59A (under surface) for young foliage, and Yellow-Green Group 147A (upper surface) and Yellow-Green Group 147B and 147C with veins of Yellow-Green Group 147A (under surface) for adult foliage. This can be compared to Green Group 139A (upper surface) for the adult foliage of the *Syringa meyeri* 'Palibin' parent, and Green Group 137A (upper surface) and Green Group 137D (under surface) for the adult foliage of the 'Bailbelle' cultivar.

*Petioles.*—Approximately 0.75 cm in length on average, approximately 0.15 cm in diameter on average. Yellow-Green Group 147C on the upper surface and Yellow-Green Group 147C blending with Red-Purple Group 59A at the axis on the under surface.

*Stems.*—Yellow-Green Group 146B on young stems and Greyed-Green Group 197A on adult wood.

*Lenticels.*—Commonly are present on stems, approximately 0.15 cm in length on average, approximately 0.1 cm in width on average, and Grey-Brown Group 199D in coloration.

Inflorescence:

*Age to flower.*—Typically the first flowers appear the second year from a rooted cutting in the field and in container production. A few flowers have been observed during the first year sometimes by late summer depending upon the time of planting.

*Time of flowering.*—Typically mid- to late-May at the indicated location, and commonly after the 'Bailbelle' cultivar. Such flowering commonly is after many other flowering shrubs have finished blooming.

*Buds.*—In a thyrse, commonly approximately 173 buds per thyrse on average, closed funnel-form, red purple, Red-Purple Group 70A, (upper surface) and Red-Purple Group 71B (under surface). The length commonly is 1.5 cm and width is approximately 0.4 cm on average.

*Flower arrangement.*—Densely packed in panicles approximately 8 to 9 cm in length and approximately 4 to 5 cm in width. Weather conditions have been observed to influence the number of buds that open. Commonly approximately 95 percent of the buds per panicle open to form flowers. Accordingly, the number of open flowers per panicle commonly is approximately 160 to 165. However, when weather conditions are cool, substantially all buds of a panicle have been observed to open to form flowers.

*Flower configuration.*—Tubular with four petal lobes at the end (as illustrated).

*Flower size.*—Approximately 1.0 cm in length and approximately 0.65 cm in diameter at the widest point.

*Flower color.*—When first opening the petals are red purple, Red-Purple Group 70A, with Red-Purple Group 69A at the margin (upper surface) and Red-Purple Group 70B with Red-Purple Group 69B and 69C at the margin (under surface). When blooming the petals are Red-Purple Group 70C with Red-Purple Group 69A at the margin (upper surface) and red purple, Red-Purple Group 70B with Red-Purple Group 69B and 69C at the margin (under surface). At the end of blooming the petals are Red-Purple Group 75A (upper surface) and Red-Purple Group 74D (under surface).

*Stamens.*—Two per flower, and near Red-Purple Group 68A with some near White Group 155D in coloration.

*Filaments.*—Red-Purple Group 62D in coloration.

*Anthers.*—Red-Purple Group 64D in coloration.

*Pollen.*—Present in a sparse quantity.

*Pistil.*—Approximately 0.4 cm in length and one per flower.

*Style.*—Red-Purple Group 62C in coloration.

*Stigma.*—Yellow-Green Group 150D in the absence of pollen and Yellow-Green Group 154D with pollen.

*Calyx.*—Cup-shaped with an entire lobe, one per flower, rugose, approximately 0.2 cm in size, initially Yellow-Green Group 149D in coloration and changing with maturity to Red-Purple Group 62B with highlights of Red-Purple Group 63D.

*Fragrance.*—Intense spicy lilac.

*Flower duration.*—Approximately 5 to 7 days on the plant.

*Seeds.*—None observed during observations to date.

Hardiness: Can be grown in U.S.D.A. Hardiness Zone Nos. 4 to 7.

Culture: Similar to the Dwarf Korean Lilac. Prefers well-drained soil and a sunny growing location. Generally does not well tolerate poorly drained growing conditions.

Disease/pest resistance: Has proven to be relatively free of disease and insect problems during observations to date.

Landscape usage: Provides a hardy highly ornamental fragrant shrub having a distinctive blossom coloration that can be grown as a specimen plant or in a mass planting. Can be grown as a foundation planting or as an informal hedge.

I claim:

1. A new and distinct *Syringa meyeri*×*Syringa microphylla* plant having the following combination of characteristics:

(a) exhibits a rounded uniform compact growth habit, (b) forms attractive trusses of fragrant red purple blossoms in late spring that fade to lavender pink, (c) is relatively free of insect and disease problems, and (d) is well-suited for growing as a distinctive ornamental shrub in the landscape;

substantially as illustrated and described.

* * * * *